(12) United States Patent
Aoyama

(10) Patent No.: US 11,744,437 B2
(45) Date of Patent: Sep. 5, 2023

(54) MEDICAL IMAGE PROCESSING SYSTEM

(71) Applicant: FUJIFILM Corporation, Tokyo (JP)

(72) Inventor: Tatsuya Aoyama, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 584 days.

(21) Appl. No.: 17/035,936

(22) Filed: Sep. 29, 2020

(65) Prior Publication Data
US 2021/0007578 A1 Jan. 14, 2021

Related U.S. Application Data

(63) Continuation of application No. PCT/JP2019/015757, filed on Apr. 11, 2019.

(30) Foreign Application Priority Data

Apr. 23, 2018 (JP) ................................ 2018-082158

(51) Int. Cl.
*G06T 7/80* (2017.01)
*A61B 1/00* (2006.01)
(Continued)

(52) U.S. Cl.
CPC ...... *A61B 1/00006* (2013.01); *A61B 1/00009* (2013.01); *A61B 1/05* (2013.01);
(Continued)

(58) Field of Classification Search
CPC ... A61B 1/00006; A61B 1/00009; A61B 1/05; A61B 1/063; A61B 1/00186;
(Continued)

(56) References Cited

U.S. PATENT DOCUMENTS 11,147,438 B2 * 10/2021 Kamee ................ A61B 1/0655
2011/0050918 A1   3/2011 Tachi
2013/0265401 A1   10/2013 Igarashi et al.

FOREIGN PATENT DOCUMENTS

EP           3222194 A1    9/2017
JP        2011-055038 A    3/2011
(Continued)

OTHER PUBLICATIONS

An Office Action; "Notice of Reasons for Refusal", mailed by the Japanese Patent Office dated Jul. 13, 2021, which corresponds to Japanese Patent Application No. 2020-516211 and is related to U.S. Appl. No. 17/035,936; with English language translation.
(Continued)

*Primary Examiner* — Charlotte M Baker
(74) *Attorney, Agent, or Firm* — Studebaker & Brackett PC

(57) ABSTRACT

Provided is a medical image processing system that can stably control the light emission amount of narrow-band light of a short wavelength in a case where the narrow-band light of the short wavelength is used for illumination of an observation target. A light source circuit emits specific narrow-band light of a short wavelength. An image sensor includes a first pixel group including a B pixel and a second pixel group including a G pixel. The B pixel has a higher sensitivity to the specific narrow-band light than the G pixel. The G pixel has a sensitivity to light in a green band and the specific narrow-band light. The light source control unit controls the light emission amount of the specific narrow-band light on the basis of a pixel value of the B pixel and a pixel value of the G pixel.

20 Claims, 12 Drawing Sheets

(51) Int. Cl.
*A61B 1/05* (2006.01)
*A61B 1/06* (2006.01)

(52) U.S. Cl.
CPC ............... *A61B 1/063* (2013.01); *G06T 7/80* (2017.01); *G06T 2207/10068* (2013.01)

(58) Field of Classification Search
CPC ....... A61B 1/0638; A61B 1/0684; G06T 7/80; G06T 2207/10068
USPC ........................................................ 382/274
See application file for complete search history.

(56) References Cited

FOREIGN PATENT DOCUMENTS

| | | |
|---|---|---|
| JP | 2016-174921 A | 10/2016 |
| WO | 2013/145410 A1 | 10/2013 |
| WO | 2016/080130 A1 | 5/2016 |

OTHER PUBLICATIONS

International Search Report issued in PCT/JP2019/015757; dated Jun. 18, 2019.
International Preliminary Report on Patentability and Written Opinion issued in PCT/JP2019/015757; dtaed Oct. 27, 2020.

* cited by examiner

FIG. 15

| G | R | G | R | G | R |
|---|---|---|---|---|---|
| B | G | B | G | B | G |
| G | R | G | R | G | R |
| B | G | B | G | B | G |
| G | R | G | R | G | R |
| B | G | B | G | B | G |

FIG. 16

| G11 | R12 | G13 |
|---|---|---|
| B21 | G22 | B23 |
| G31 | R32 | G33 |

SP

MEDICAL IMAGE PROCESSING SYSTEM

CROSS-REFERENCE TO RELATED APPLICATIONS

This application is a Continuation of PCT International Application No. PCT/JP2019/015757 filed on Apr. 11, 2019, which claims priority under 35 U.S.C § 119(a) to Japanese Patent Application No. 2018-082158 filed on Apr. 23, 2018. Each of the above application(s) is hereby expressly incorporated by reference, in its entirety, into the present application.

BACKGROUND OF THE INVENTION

1. Field of the Invention

The present invention relates to a medical image processing system that controls the light emission amount of narrow-band light of a short wavelength used for illuminating an observation target.

2. Description of the Related Art

In the medical field, an endoscope system comprising a light source device, an endoscope, and a processor device is widely used. In the endoscope system, an observation target is irradiated with illumination light from the endoscope, and an image of the observation target is displayed on the monitor on the basis of an RGB image signal obtained by imaging the observation target illuminated with the illumination light with an image sensor of the endoscope.

Further, in diagnosis using an endoscope, since the brightness of the observation target changes as a distance between a distal end portion of the endoscope having the image sensor and the observation target changes, the light emission amount of illumination light is controlled according to a change in brightness information of the observation target. In the case of using light in a plurality of red bands (540 nm, 600 nm, and 630 nm) as illumination light in order to observe a blood vessel at a deep position in a mucosal tissue, the brightness information (dimming reference signal) of the observation target corresponding to the light in the plurality of red bands is calculated to control the light emission amount of the illumination light (see WO2013/145410A).

SUMMARY OF THE INVENTION

In endoscopic diagnosis in recent years, in order to observe specific structures such as surface blood vessels and red blood cells, narrow-band light of a short wavelength having a center wavelength of 410 nm to 450 nm is being used for illumination of an observation target. Also in a case of using such an observation target illuminated with narrow-band light of a short wavelength, it is required to accurately calculate the brightness information of the observation target and to stably control the light emission amount of the narrow-band light of the short wavelength.

An object of the invention is to provide a medical image processing system that can stably control the light emission amount of narrow-band light of a short wavelength in a case where the narrow-band light of the short wavelength is used for illumination of an observation target.

A medical image processing system according to an aspect of the invention comprises a light source unit that emits specific narrow-band light of a short wavelength, an image sensor that images an observation target illuminated with the specific narrow-band light, the image sensor including a first pixel group including a first pixel and a second pixel group including at least a second pixel, and a light source control unit that controls a light emission amount of the specific narrow-band light. The first pixel has a higher sensitivity to the specific narrow-band light than the second pixel, the second pixel has a sensitivity to first long-wavelength light of a longer wavelength than the specific narrow-band light and the specific narrow-band light, and the light source control unit controls the light emission amount of the specific narrow-band light on the basis of a pixel value of the first pixel obtained in the first pixel and a pixel value of the second pixel obtained in the second pixel.

It is preferable that the second pixel group includes a third pixel having a sensitivity to broadband illumination light including the specific narrow-band light and the first long-wavelength light, and the light source control unit controls the light emission amount of the specific narrow-band light on the basis of a pixel value of the third pixel in addition to the pixel value of the first pixel and the pixel value of the second pixel. It is preferable that the second pixel group includes a fourth pixel having a sensitivity to second long-wavelength light of a longer wavelength than the first long-wavelength light and the specific narrow-band light, and the light source control unit controls the light emission amount of the specific narrow-band light on the basis of a pixel value of the fourth pixel in addition to the pixel value of the first pixel and the pixel value of the second pixel.

It is preferable that the medical image processing system further comprises a brightness information calculation unit that calculates brightness information indicating brightness of the observation target on the basis of the pixel value of the first pixel multiplied by a brightness adjustment coefficient for the first pixel and the pixel value of the second pixel multiplied by a brightness adjustment coefficient for the second pixel, the light source control unit controls the light emission amount of the specific narrow-band light on the basis of the brightness information, and a ratio between the brightness adjustment coefficient for the first pixel and the brightness adjustment coefficient for the second pixel is determined on the basis of a short-wavelength sensitivity to short-wavelength light including the specific narrow-band light in the sensitivity of the first pixel and the short-wavelength sensitivity of the second pixel.

It is preferable that the short-wavelength sensitivity of the second pixel is 10% or more of a maximum sensitivity of the second pixel, or 10% or more of the short-wavelength sensitivity of the first pixel. It is preferable that the short-wavelength sensitivity of the second pixel is 35% or less of a maximum sensitivity of the second pixel, or 35% or less of the short-wavelength sensitivity of the first pixel.

It is preferable that the medical image processing system further comprises a brightness information calculation unit that calculates brightness information indicating brightness of the observation target on the basis of the pixel value of the first pixel multiplied by a brightness adjustment coefficient for the first pixel, the pixel value of the second pixel multiplied by a brightness adjustment coefficient for the second pixel, and the pixel value of the third pixel multiplied by a brightness adjustment coefficient for the third pixel, the light source control unit controls the light emission amount of the specific narrow-band light on the basis of the brightness information, and a ratio between the brightness adjustment coefficient for the first pixel, the brightness adjustment coefficient for the second pixel, and the brightness adjustment coefficient for the third pixel is determined on the basis of a short-wavelength sensitivity to short-wavelength light including the specific narrow-band light in the sensitivity of the first pixel, the short-wavelength sensitivity of the second pixel, and the short-wavelength sensitivity of the third pixel.

It is preferable that the medical image processing system further comprises a brightness information calculation unit that calculates brightness information indicating brightness of the observation target on the basis of the pixel value of the first pixel multiplied by a brightness adjustment coefficient for the first pixel, the pixel value of the second pixel multiplied by a brightness adjustment coefficient for the second pixel, and the pixel value of the fourth pixel multiplied by a brightness adjustment coefficient for the fourth pixel, the light source control unit controls the light emission amount of the specific narrow-band light on the basis of the brightness information, and a ratio between the brightness adjustment coefficient for the first pixel, the brightness adjustment coefficient for the second pixel, and the brightness adjustment coefficient for the fourth pixel is determined on the basis of a short-wavelength sensitivity to short-wavelength light including the specific narrow-band light in the sensitivity of the first pixel, the short-wavelength sensitivity of the second pixel, and the short-wavelength sensitivity of the fourth pixel.

It is preferable that the number of pixels of the second pixel group is greater than the number of pixels of the first pixel group. It is preferable that a center wavelength of the specific narrow-band light is included in a range of 400 nm to 450 nm, and a half-width of the specific narrow-band light is 40 nm or less.

According to the invention, it is possible to stably control the light emission amount of narrow-band light of a short wavelength in a case where the narrow-band light of the short wavelength is used for illumination of an observation target.

BRIEF DESCRIPTION OF THE DRAWINGS

FIG. 15 is an explanatory diagram showing an image sensor having a Bayer array.
FIG. 16 is an explanatory diagram used for describing a method of calculating a pixel value of a B pixel at a G pixel position in the image sensor having a Bayer array.

DESCRIPTION OF THE PREFERRED EMBODIMENTS

First Embodiment

Figure 1:
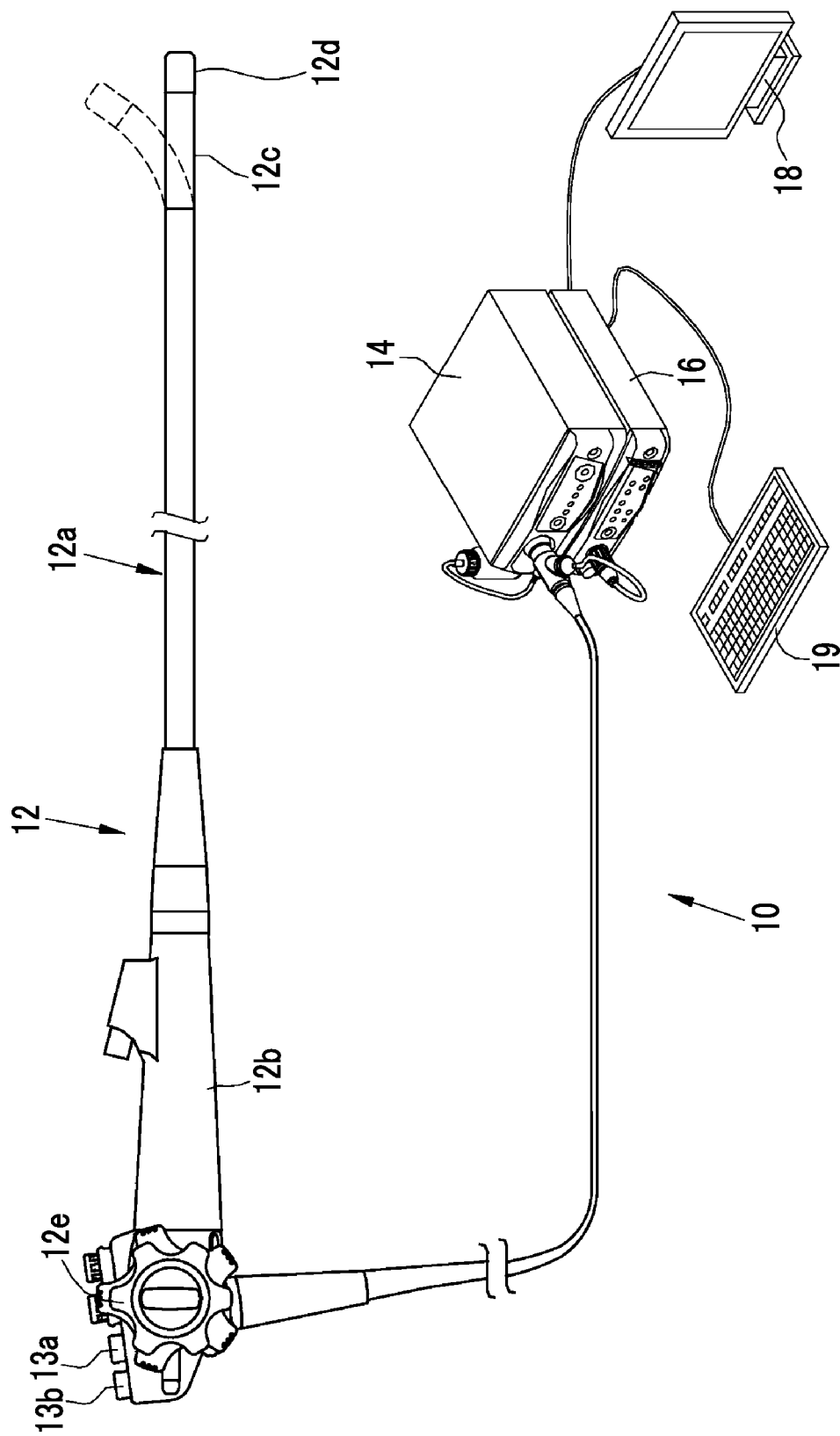
FIG. 1 is an external view of an endoscope system.

As shown in FIG. 1, an endoscope system 10 according to a first embodiment has an endoscope 12, a light source device 14, a processor device 16, a monitor 18, and a user interface 19. The endoscope 12 is optically connected to the light source device 14 and electrically connected to the processor device 16. The endoscope 12 has an insertion part 12a to be inserted into a subject, an operation part 12b provided in a proximal end portion of the insertion part 12a, and a bendable portion 12c and a distal end portion 12d that are provided on the distal end side of the insertion part 12a. The bendable portion 12c is bent by operating an angle knob 12e of the operation part 12b. With the bending operation, the distal end portion 12d is directed in a desired direction. The user interface 19 includes a mouse or the like in addition to the illustrated keyboard.

In addition to the angle knob 12e, a mode switching SW 13a and a still image acquisition instruction part 13b are provided in the operation part 12b. The mode switching SW 13a is used to switch among a normal observation mode, a special observation mode, and a short wavelength observation mode. The normal observation mode is a mode in which an observation target is illuminated with normal light such as white light (see FIGS. 9 and 10) and a normal image is displayed on the monitor 18. The special observation mode is a mode in which an observation target is illuminated with special light such as blue narrow-band light, and a special observation image in which a structure such as a blood vessel at a specific depth is emphasized is displayed on the monitor 18. The short wavelength observation mode is a mode in which a short wavelength observation image showing a structure that can be observed with specific narrow-band light of a short wavelength (corresponding to violet light V described later) is displayed on the monitor 18 by using the specific narrow-band light of the short wavelength for illumination of an observation target. As the mode switching unit for switching the mode, a foot switch may be used in addition to the mode switching SW 13a.

The processor device 16 is electrically connected to the monitor 18 and the user interface 19. The monitor 18 outputs and displays image information and the like. The user interface 19 functions as a user interface (UI) that receives input operations such as function settings. An external recording unit (not shown) for recording image information and the like may be connected to the processor device 16.

Figure 2:
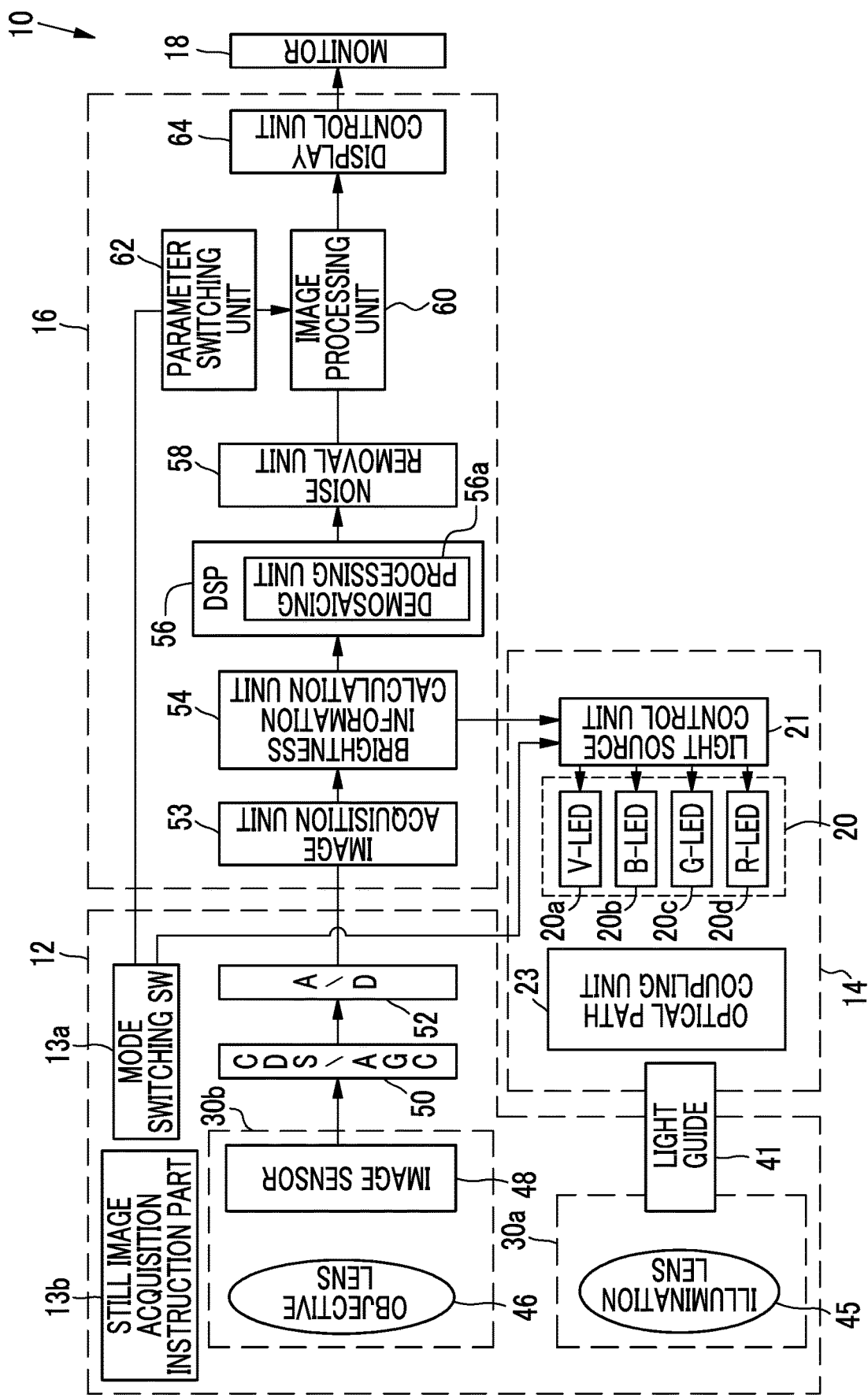
FIG. 2 is a block diagram showing a function of the endoscope system.

As shown in FIG. 2, the light source device 14 has a light source unit 20, a light source control unit 21, and an optical path coupling unit 23. The light source unit 20 has a violet light emitting diode (V-LED) 20a, a blue light emitting diode (B-LED) 20b, a green light emitting diode (G-LED) 20c, and a red light emitting diode (R-LED) 20d. The light source control unit 21 controls driving of the LEDs 20a to 20d. The optical path coupling unit 23 couples optical paths of light of four colors emitted from the LEDs 20a to 20d of four colors. The light coupled by the optical path coupling unit 23 is emitted into the subject through a light guide 41 and an illumination lens 45 which are inserted into the insertion part 12a. A laser diode (LD) may be used instead of the LED.

Figure 3:
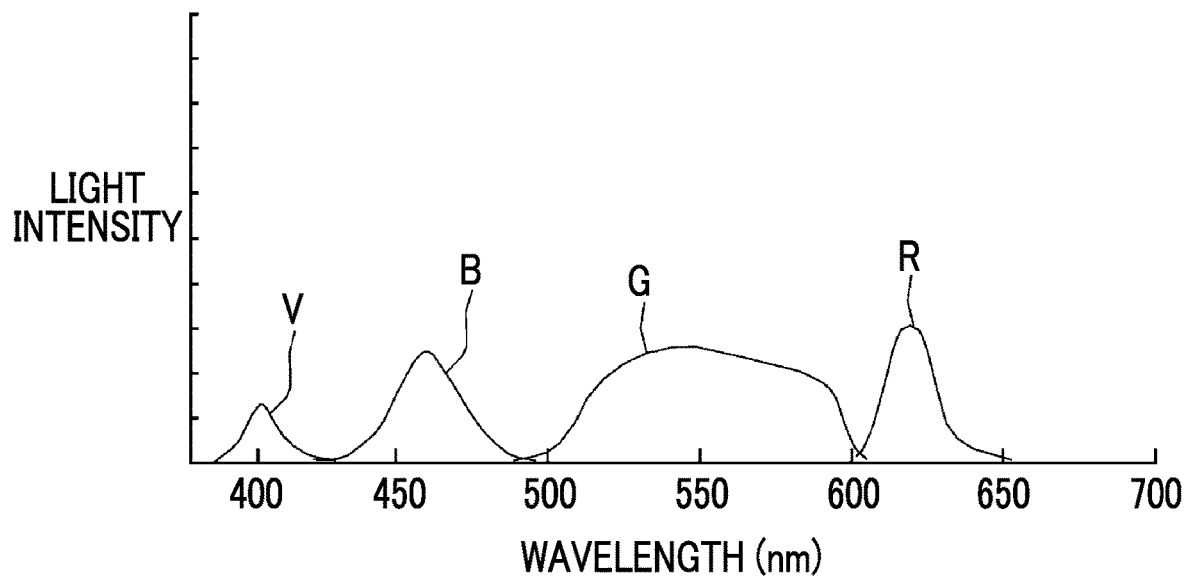
FIG. 3 is a graph showing spectra of violet light V, blue light B, green light G, and red light R.

As shown in FIG. 3, the V-LED 20a generates violet light V having a center wavelength of 400 nm to 450 nm (for example, 405 nm) and a half-width of 40 nm or less. The B-LED 20b generates blue light B having a center wavelength of 450 nm to 500 nm (for example, 460 nm) and a half-width of 40 nm or less. The G-LED 20c generates green light G having a wavelength range of 480 nm to 600 nm. The R-LED 20d generates red light R having a center wavelength of 620 nm to 630 nm and a wavelength range of 600 nm to 650 nm.

Figure 4:
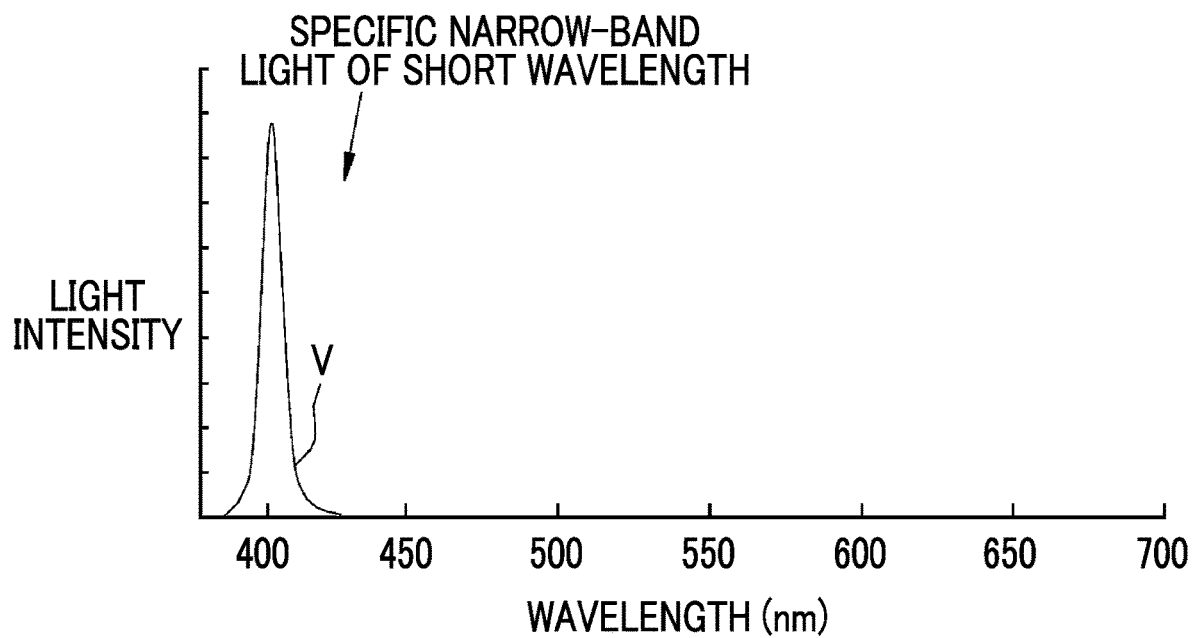
FIG. 4 is a graph showing a spectrum of specific narrow-band light of a short wavelength.

The light source control unit 21 performs control to turn on the V-LED 20a, the B-LED 20b, the G-LED 20c, and the R-LED 20d in the normal observation mode and the special observation mode. In the normal observation mode, the light source control unit 21 controls each of the LEDs 20a to 20d so as to emit normal light in which a light intensity ratio among the violet light V, the blue light B, the green light G, and the red light R is Vc:Bc:Gc:Rc. In the special observation mode, the light source control unit 21 controls each of the LEDs 20a to 20d so as to emit special light in which the light intensity ratio among the violet light V, the blue light B, the green light G, and the red light R is Vs:Bs:Gs:Rs. It is preferable that the special light can emphasize a structure such as a blood vessel at a specific depth. Further, as shown in FIG. 4, in the short wavelength observation mode, the light source control unit 21 controls each of the LEDs 20a to 20d so as to emit the violet light V which is the specific narrow-band light of the short wavelength.

In the present specification, the light intensity ratio includes a case where the ratio of at least one semiconductor light source is 0 (zero). Accordingly, a case where any one or two or more of the semiconductor light sources are not turned on is included. For example, as in the case where the light intensity ratio among the violet light V, the blue light B, the green light G, and the red light R is 1:0:0:0, even in a case where only one of the semiconductor light sources is turned on and the other three are not turned on, it is assumed that a light intensity ratio is present.

Further, the light source control unit 21 controls the light emission amount of the illumination light emitted from each of the LEDs 20a to 20d on the basis of brightness information sent from a brightness information calculation unit 54 of the processor device 16. In the case of the normal observation mode, the light source control unit 21 controls the light emission amount of the normal light so as to satisfy the following Equation A) on the basis of brightness information for the normal observation mode. For example, in a case where "brightness information for normal observation mode/256" is lower than a specified number, control is performed to increase the light emission amount of the normal light. In contrast, in a case where "brightness information for normal observation mode/256" is higher than a specified number, control is performed to reduce the light emission amount of the normal light.

Brightness information for normal observation mode/ 256=specified number     Equation A)

In the case of the special observation mode, the light source control unit 21 controls the light emission amount of the special light so as to satisfy the following Equation B) on the basis of brightness information for the special observation mode. For example, in a case where "(brightness information for special observation mode+addition coefficient for special observation mode)/256" is lower than a specified number, control is performed to increase the light emission amount of the special light. In contrast, in a case where "(brightness information for special observation mode+addition coefficient for special observation mode)/ 256" is higher than a specified number, control is performed to reduce the light emission amount of the special light.

(Brightness information for special observation mode+addition coefficient for special observation mode)/256=specified number     Equation B)

In the case of the short wavelength observation mode, the light source control unit 21 controls the light emission amount of the specific narrow-band light of the short wavelength so as to satisfy the following Equation C) on the basis of brightness information for the short wavelength observation mode. For example, in a case where "(brightness information for short wavelength observation mode+addition coefficient for short wavelength observation mode)/ 256" is lower than a specified number, control is performed to increase the light emission amount of the specific narrow-band light of the short wavelength. In contrast, in a case where "(brightness information for short wavelength observation mode+addition coefficient for short wavelength observation mode)/256" is higher than a specified number, control is performed to reduce the light emission amount of the specific narrow-band light of the short wavelength.

(Brightness information for short wavelength observation mode+addition coefficient for short wavelength observation mode)/256=specified number     Equation C)

The brightness information for the short wavelength observation mode is calculated by including a G image signal having a signal value corresponding to the specific narrow-band light in addition to a B image signal, and thus it is possible to stably control the light emission amount of the specific narrow-band light. For example, in a case where a blue-related dye is scattered on the observation target, when the brightness information for the short wavelength observation mode is calculated on the basis of only the B image signal, it is difficult to stably control the light emission amount of the specific narrow-band light of the short wavelength. As in the present embodiment, the brightness information for the short wavelength observation mode is calculated on the basis of the G image signal in addition to the B image signal, so that it is less likely to be affected by the blue-related dye. Therefore, it is possible to stably control the light emission amount of the specific narrow-band light of the short wavelength.

Also in a case where the brightness information for the short wavelength observation mode is calculated on the basis of the B image signal, the G image signal, and a W image signal, the W image signal is less likely to be affected by the blue-related dye. Therefore, the light emission amount of the specific narrow-band light can be stably controlled according to the brightness information based on the B image signal, the G image signal, and the W image signal. Similarly, also in a case where the brightness information for the short wavelength observation mode is calculated on the basis of the B image signal, the G image signal, and an R image signal, the R image signal is less likely to be affected by the blue-related dye. Therefore, the light emission amount of the specific narrow-band light can be stably controlled according to the brightness information based on the B image signal, the G image signal, and the R image signal.

As shown in FIG. 2, the light guide 41 is built in the endoscope 12 and a universal cord (a cord that connects the endoscope 12 to the light source device 14 and the processor device 16), and propagates the light coupled by the optical path coupling unit 23 to the distal end portion 12d of the endoscope 12. It is possible to use a multi-mode fiber as the light guide 41. As an example, it is possible to use a small-diameter fiber cable of which a core diameter is 105 μm, a cladding diameter is 125 μm, and a diameter including a protective layer as an outer skin is φ0.3 mm to φ0.5 mm.

An illumination optical system 30a and an imaging optical system 30b are provided in the distal end portion 12d of the endoscope 12. The illumination optical system 30a has the illumination lens 45, and the observation target is irradiated with the light from the light guide 41 through the illumination lens 45. The imaging optical system 30b has an objective lens 46 and an image sensor 48. The reflected light from the observation target is incident on the image sensor 48 through the objective lens 46. In this manner, a reflected image of the observation target is formed on the image sensor 48.

Figures 5, 6:
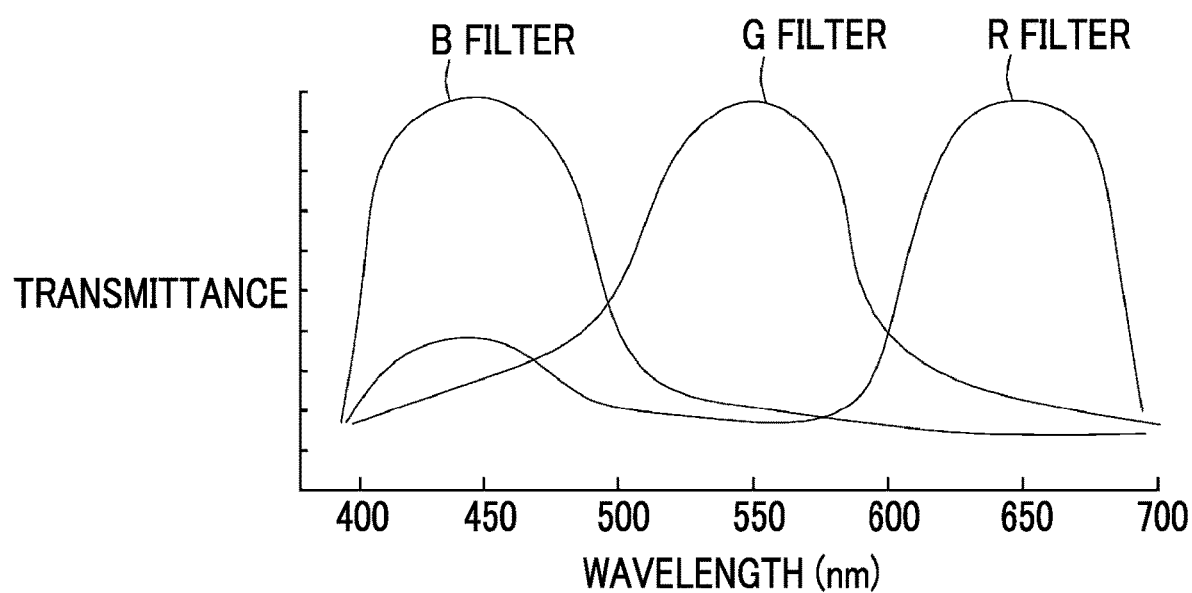
FIG. 5 is an explanatory diagram showing R pixels (R), G pixels (G), B pixels (B), and W pixels (W) provided in an image sensor.
FIG. 6 is a graph showing spectral transmittances of a B filter, a G filter, and an R filter included in an image sensor of the present embodiment.

The image sensor 48 is a color image sensor and captures a reflected image of the subject to output an image signal. The image sensor 48 is preferably a charge coupled device (CCD) image sensor, a complementary metal-oxide semiconductor (CMOS) image sensor, or the like. The image sensor 48 used in the invention is a color image sensor for obtaining RGBW image signals of four colors of red (R), green (G), blue (B), and white (W). That is, as shown in FIG. 5, the image sensor 48 comprises an R pixel (fourth pixel) provided with an R filter, a G pixel (second pixel) provided with a G filter, a B pixel (first pixel) provided with a B filter, and a W pixel (third pixel) provided with a W filter. The image sensor 48 is divided into two pixel groups of a first pixel group and a second pixel group, and the number of pixels of the second pixel group is greater than the number of pixels of the first pixel group. The first pixel group includes B pixels, and the second pixel group includes G pixels, R pixels, and W pixels.

In the image sensor 48, the W pixels are arranged in a checkered pattern. Further, for the signal obtained by the image sensor 48 in the short wavelength observation mode, in order to improve the resolution, as shown in demosaicing processing described later, by giving the G pixel a certain level or more of a sensitivity to the specific narrow-band light and using the correlation between the W pixel and the G pixel, a signal of the specific narrow-band light can be obtained even at a G pixel position. Similarly, by giving the R pixel a certain level or more of a sensitivity to the specific narrow-band light and using a correlation between the W pixel and the R pixel, a signal of the specific narrow-band light can be obtained even at an R pixel position.

Figure 7:
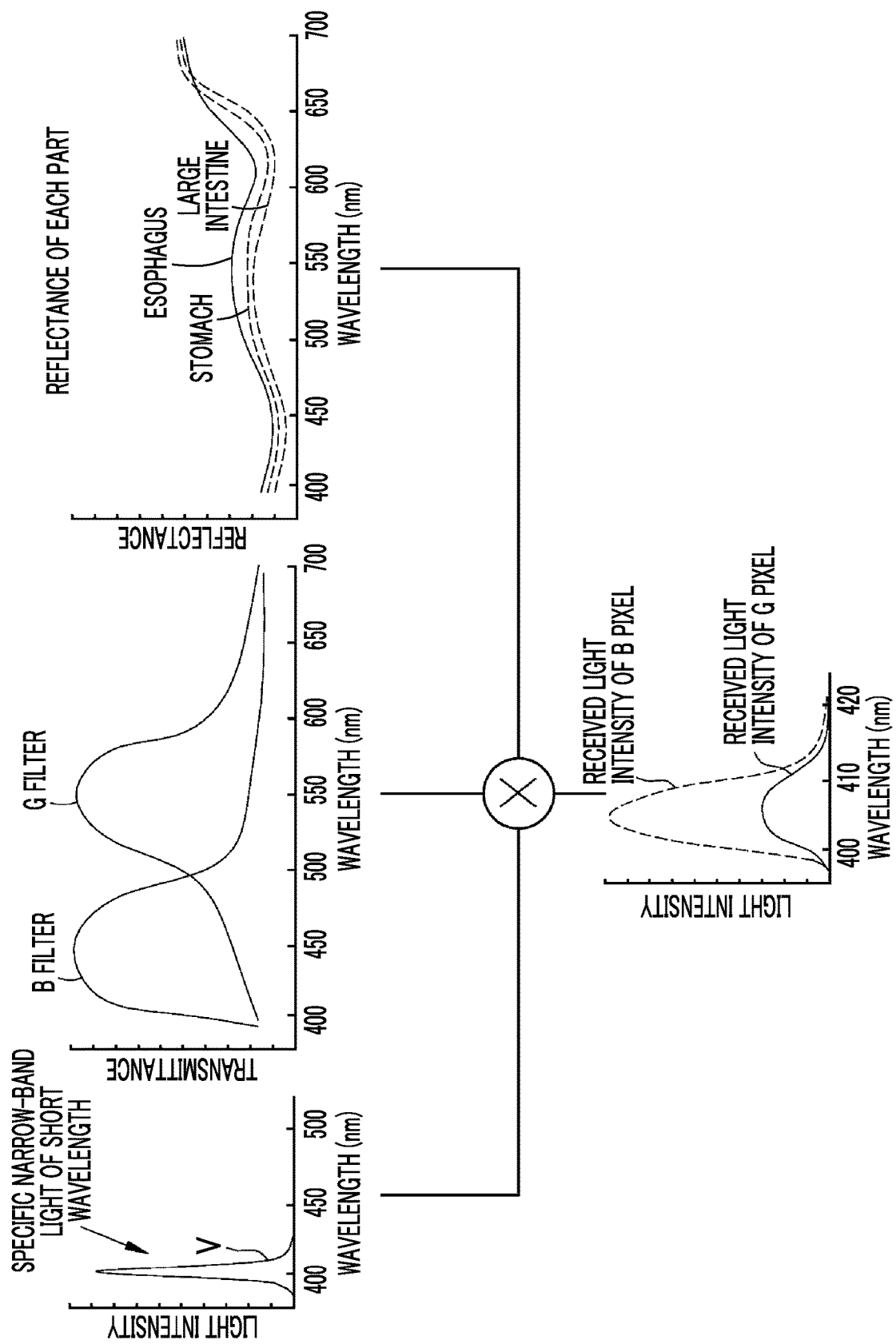
FIG. 7 is an explanatory diagram showing received light intensities of a B pixel and a G pixel in a case where an esophagus is illuminated with specific narrow-band light of a short wavelength.

As described above, in order to obtain a signal of specific narrow-band light at the G pixel position during illumination with specific narrow-band light of a short wavelength, as shown in FIG. 6, the transmittance of the G filter is set so that the G pixel has not only the sensitivity to light in a green band (first long-wavelength light) of 500 nm to 600 nm, but also the short-wavelength sensitivity to short-wavelength light (a wavelength band is 450 nm or less, for example, 400 nm to 450 nm) including the specific narrow-band light of the short wavelength. In this manner, as shown in FIG. 7, in a case where the specific narrow-band light, the transmittance of the G filter, and the reflectance of each part (the reflectance of the "esophagus" is used in the case of FIG. 7, and the reflectances of the stomach and large intestine are shown by the dotted line) are multiplied, a received light intensity corresponding to the wavelength range of the specific narrow-band light is obtained as a received light intensity of the G pixel. A received light intensity of the B pixel is obtained by multiplying the specific narrow-band light, the transmittance of the B filter (blue band of 400 nm to 500 nm), and the reflectance of each part, and is a constant multiple of the intensity value of the received light intensity of the G pixel.

In a case where the signal value obtained by the G pixel is small, the influence of noise increases, and the image quality of the image after the demosaicing processing deteriorates. Therefore, for example, a short-wavelength sensitivity of the G pixel is preferably 10% or more of the maximum sensitivity of the G pixel at 400 nm to 450 nm. That is, in the G filter, the transmittance at 400 nm to 450 nm is preferably 10% or more of the transmittance at the wavelength range (for example, 540 nm to 560 nm) corresponding to the maximum sensitivity of the G pixel. Alternatively, the short-wavelength sensitivity of the G pixel is preferably 10% or more of a short-wavelength sensitivity of the B pixel. That is, in the G filter, the transmittance at 400 nm to 450 nm is preferably 10% or more of the transmittance at 400 nm to 450 nm of the B filter. The maximum sensitivity of the G pixel refers to the sensitivity to light in the wavelength range in which the transmittance of the G color filter is equal to or higher than a certain value (for example, 70%). The same applies to the maximum sensitivity of the R pixel.

On the other hand, in a case where the short-wavelength sensitivity of the G pixel becomes too high, the color reproducibility in a normal image deteriorates. Therefore, the short-wavelength sensitivity of the G pixel is preferably 35% or less of the maximum sensitivity of the G pixel at 400 nm to 450 nm. That is, in the G filter, the transmittance at 400 nm to 450 nm is preferably 35% or less of the transmittance at the wavelength range (for example, 540 nm to 560 nm) corresponding to the maximum sensitivity of the G pixel. Alternatively, the short-wavelength sensitivity of the G pixel is preferably 35% or less of the short-wavelength sensitivity of the B pixel. That is, in the G filter, the transmittance at 400 nm to 450 nm is preferably 35% or less of the transmittance at 400 nm to 450 nm of the B filter.

Figure 8:
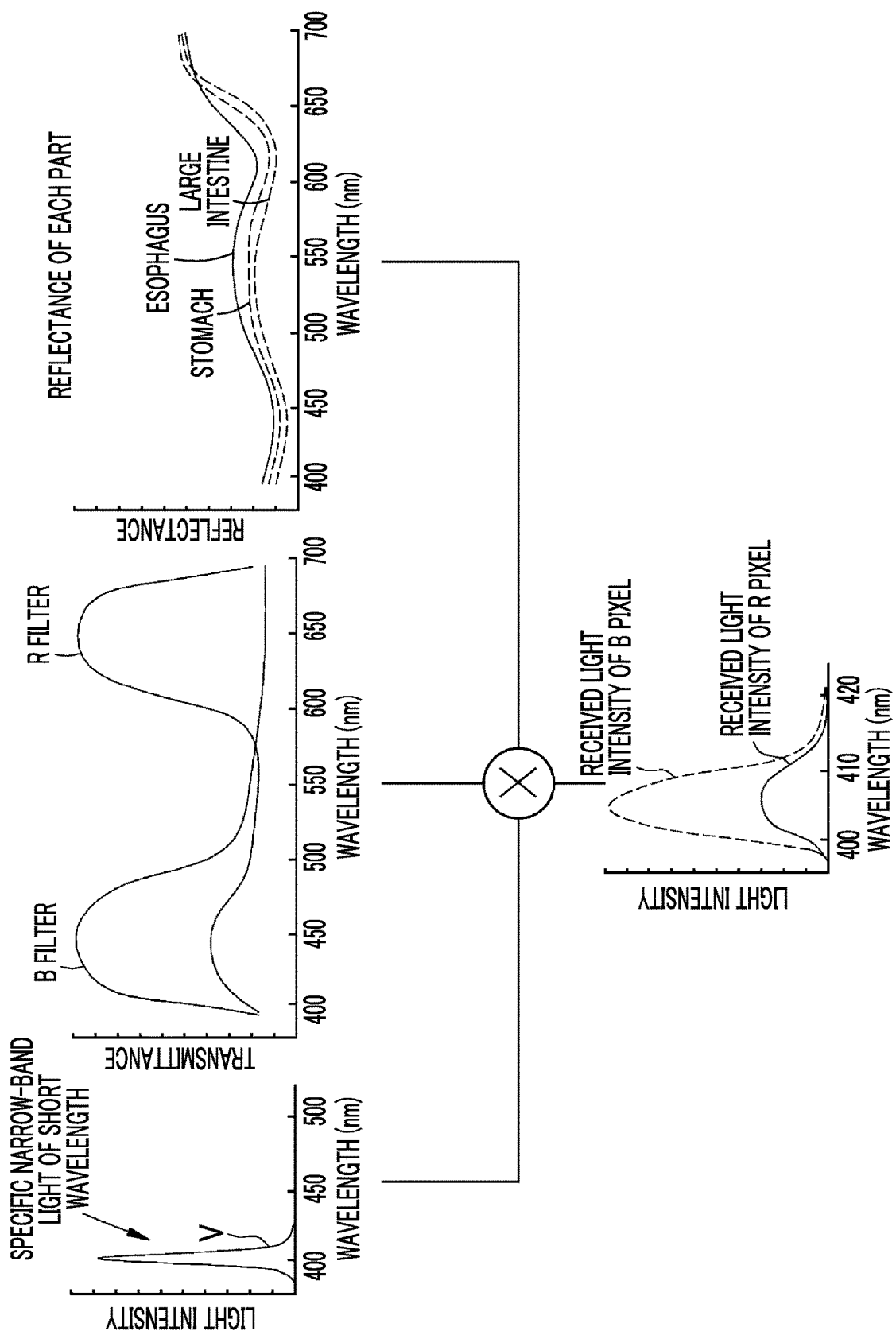
FIG. 8 is an explanatory diagram showing received light intensities of a B pixel and an R pixel in a case where an esophagus is illuminated with specific narrow-band light of a short wavelength.

Further, in order to obtain a signal of specific narrow-band light at the R pixel position during illumination with specific narrow-band light of a short wavelength, as shown in FIG. 6, the transmittance of the R filter is set so that the R pixel has not only the sensitivity to light in a red band (second long-wavelength light) of 600 nm to 700 nm, but also the short-wavelength sensitivity to short-wavelength light (400 nm to 450 nm) including the specific narrow-band light of the short wavelength. In this manner, as shown in FIG. 8, in a case where the specific narrow-band light, the transmittance of the R filter, and the reflectance of each part (the reflectance of the "esophagus" is used in the case of FIG. 8, and the reflectances of the stomach and large intestine are shown by the dotted line) are multiplied, a received light intensity corresponding to the wavelength range of the specific narrow-band light is obtained as a received light intensity of the R pixel. The received light intensity of the B pixel is a constant multiple of the received light intensity of the R pixel.

Here, in a case where the signal value obtained by the R pixel is small, the influence of noise increases, and the image quality of the image after the demosaicing processing deteriorates. Therefore, for example, a short-wavelength sensitivity of the R pixel is preferably 10% or more of the maximum sensitivity of the R pixel at 400 nm to 450 nm. That is, in the R filter, the transmittance at 400 nm to 450 nm is preferably 10% or more of the transmittance at the wavelength range (for example, 640 nm to 660 nm) corresponding to the maximum sensitivity of the R pixel. Alternatively, the short-wavelength sensitivity of the R pixel is preferably 10% or more of the short-wavelength sensitivity of the B pixel. That is, in the R filter, the transmittance at 400 nm to 450 nm is preferably 10% or more of the transmittance at 400 nm to 450 nm of the B filter.

On the other hand, in a case where the short-wavelength sensitivity of the R pixel becomes too high, the color reproducibility in a normal image deteriorates. Therefore, the short-wavelength sensitivity of the R pixel is preferably 35% or less of the maximum sensitivity of the R pixel at 400 nm to 450 nm. That is, in the R filter, the transmittance at 400 nm to 450 nm is preferably 35% or less of the transmittance at the wavelength range (for example, 640 nm to 660 nm) corresponding to the maximum sensitivity of the R pixel. Alternatively, the short-wavelength sensitivity of the R pixel is preferably 35% or less of the short-wavelength sensitivity of the B pixel. That is, in the R filter, the transmittance at 400 nm to 450 nm is preferably 35% or less of the transmittance at 400 nm to 450 nm of the B filter.

In the image sensor 48, since the W pixel has a spectral sensitivity to the illumination light of the broadband light from the blue band to the red band so that the W pixel includes the specific narrow-band light of the short wavelength, the light in the green band, and the light in the red band, the saturation of the pixel value is faster than other pixels such as the B pixel, the G pixel, and the R pixel. Accordingly, the sensitivity of the W pixel is set lower than the sensitivity of other pixels such as the B pixel, the G pixel, and the R pixel. Specifically, the sensitivity of the W pixel is preferably 30% to 50% with respect to the maximum sensitivity of the B pixel (for example, a sensitivity at 440 nm to 460 nm) or the maximum sensitivity of the G pixel (for example, a sensitivity at 540 nm to 560 nm).

Figure 9:
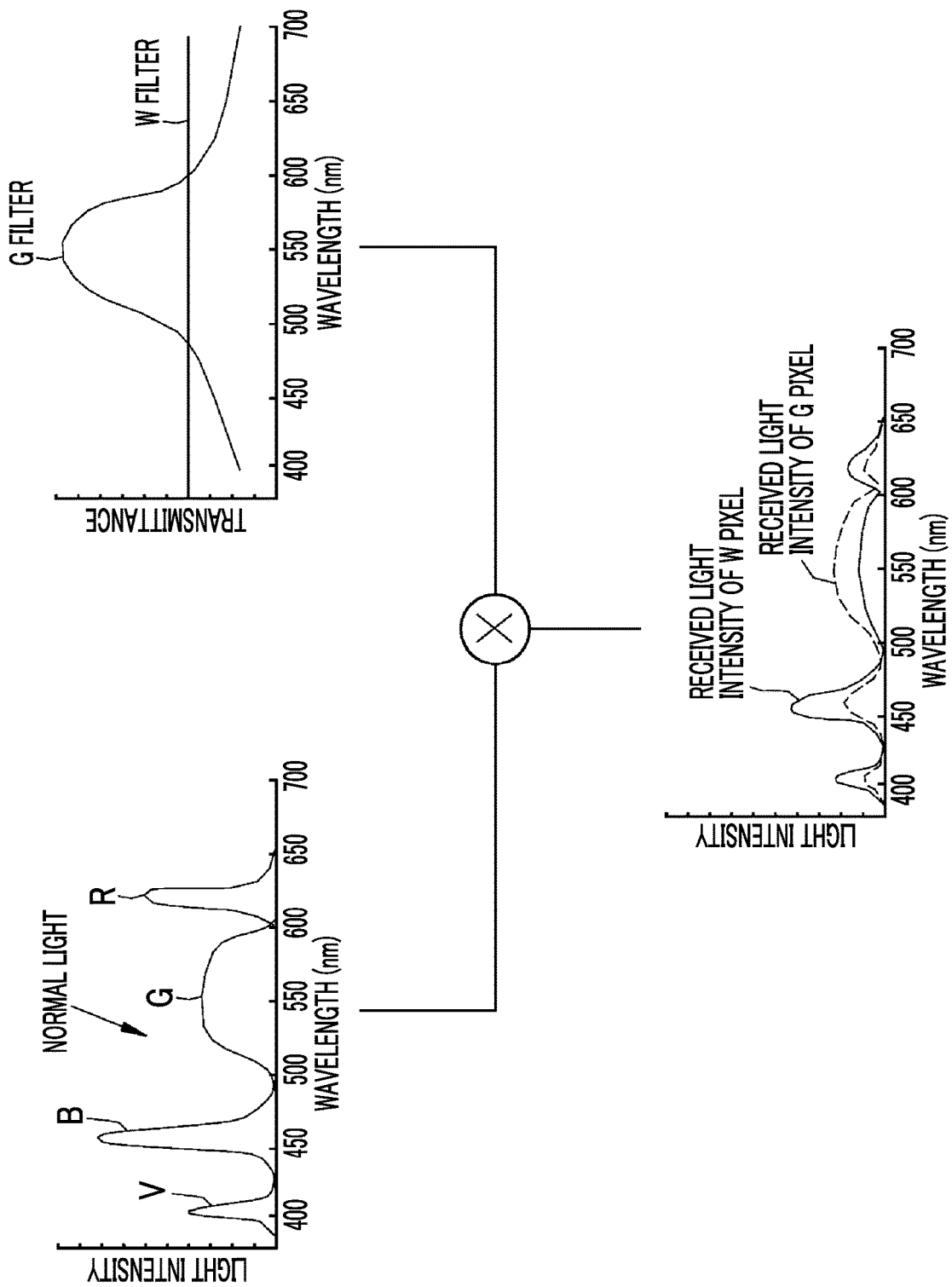
FIG. 9 is an explanatory diagram showing received light intensities of a W pixel and a G pixel in a case where an observation target is illuminated with normal light.
Figure 10:
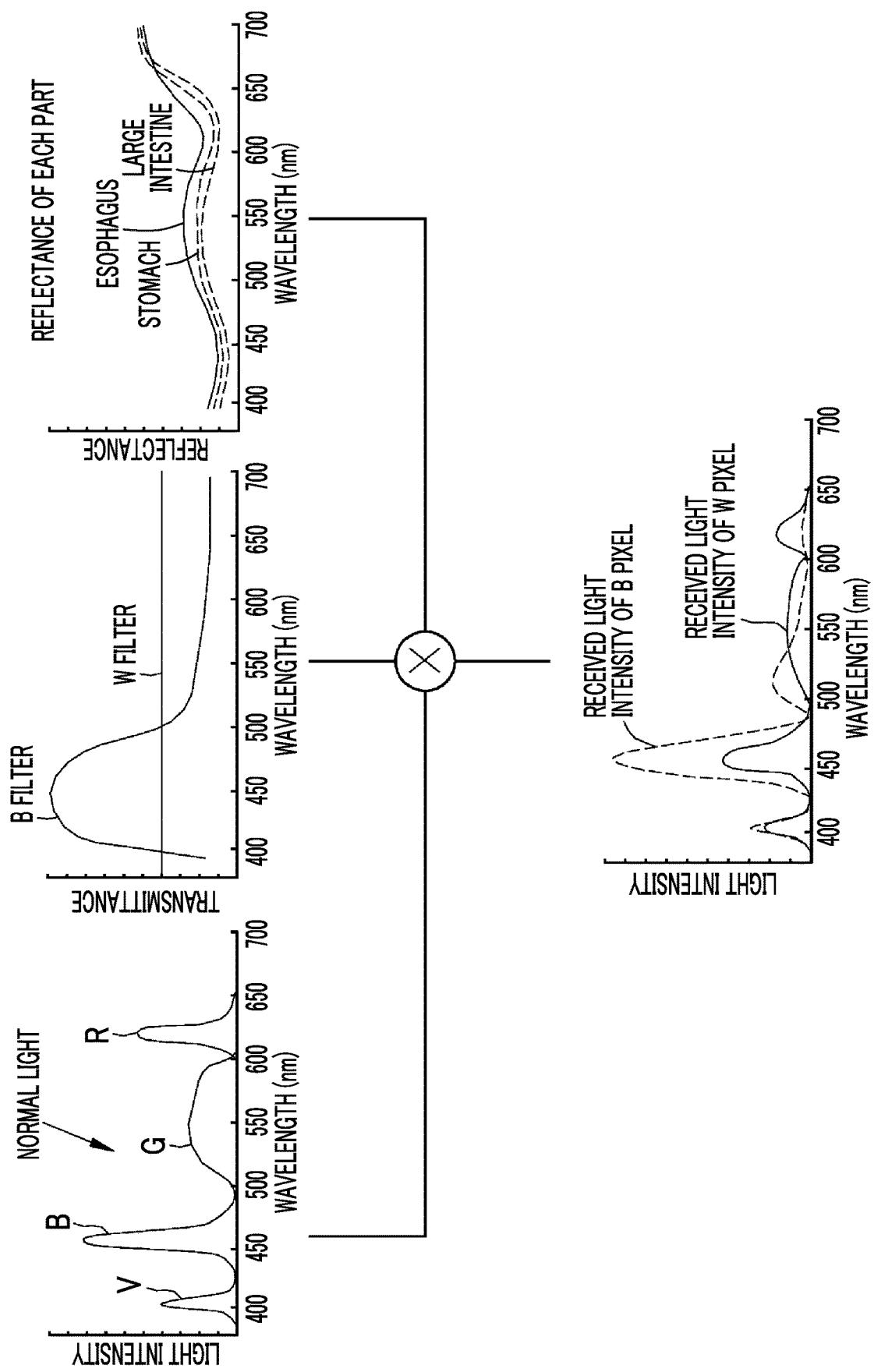
FIG. 10 is an explanatory diagram showing received light intensities of a W pixel and an R pixel in a case where an esophagus is illuminated with normal light.

For example, in the relationship regarding the sensitivity between the W pixel and the G pixel, as shown in FIG. 9, the transmittance of the W filter is set so that a received light intensity of the W pixel obtained by multiplying the light source spectrum of the normal light and the transmittance of the W filter is about 50% (for example, 45% to 55%) of the received light intensity of the G pixel obtained by multiplying the light source spectrum of normal light and the transmittance of the G filter. Alternatively, in the relationship regarding the sensitivity between the W pixel and the B pixel, as shown in FIG. 10, the transmittance of the W filter is set so that the received light intensity of the W pixel obtained by multiplying the light source spectrum of the normal light and the transmittance of the W filter is about 50% (for example, 45% to 55%) of the received light intensity of the B pixel obtained by multiplying the light source spectrum of normal light, the transmittance of the B filter, and the reflectance of the esophagus.

The image sensor 48 may be a so-called complementary color image sensor comprising complementary color filters of cyan (C), magenta (M), yellow (Y), and green (G) instead of the RGBW color image sensor. In a case of using the complementary color image sensor, since four color image signals of CMYG are output, it is necessary to convert the four color image signals of CMYG into three color image signals of RGB by complementary color-primary color conversion. The image sensor 48 may be a monochrome image sensor without a color filter.

As shown in FIG. 2, the image signal output from the image sensor 48 is transmitted to a CDS/AGC circuit 50. The CDS/AGC circuit 50 performs correlated double sampling (CDS) and auto gain control (AGC) on an image signal which is an analog signal. The image signal that has passed through the CDS/AGC circuit 50 is converted into a digital image signal by an analog/digital (A/D) converter 52. The A/D converted digital image signal is input to the processor device 16.

The processor device 16 comprises an image acquisition unit 53, the brightness information calculation unit 54, a digital signal processor (DSP) 56, a noise removal unit 58, an image processing unit 60, a parameter switching unit 62, and a display control unit 64.

The image acquisition unit 53 acquires an observation image obtained by imaging the observation target with the endoscope 12. Specifically, a digital color image signal from the endoscope 12 is input to the image acquisition unit 53 as an observation image. The color image signal is an RGBW image signal composed of an R image signal (a pixel value of an R pixel) output from the R pixel of the image sensor 48, a G image signal (a pixel value of a G pixel) output from the G pixel of the image sensor 48, a B image signal (a pixel value of a B pixel) output from the B pixel of the image sensor 48, and a W image signal (a pixel value of a W pixel) output from the W pixel of the image sensor 48.

The brightness information calculation unit 54 calculates brightness information indicating the brightness of the observation target for each observation mode on the basis of the RGBW image signal input from the image acquisition unit 53. The calculated brightness information is sent to the light source control unit 21 and is used to control the light emission amount of the illumination light. The brightness information is represented by, for example, the number of bits.

In the case of the normal observation mode, the brightness information for the normal observation mode is calculated by the following Equation K).

Brightness information for normal observation mode=brightness adjustment coefficient $kcr \times R$ image signal+brightness adjustment coefficient $kcg \times G$ image signal+brightness adjustment coefficient $kcb \times B$ image signal+brightness adjustment coefficient $kcw \times W$ image signal    Equation K)

In the case of the special observation mode, the brightness information for the special observation mode is calculated by the following Equation L).

Brightness information for special observation mode=brightness adjustment coefficient $ksr \times R$ image signal+brightness adjustment coefficient $ksg \times G$ image signal+brightness adjustment coefficient $ksb \times B$ image signal+brightness adjustment coefficient $ksw \times W$ image signal    Equation L)

In the case of the short wavelength observation mode, the brightness information for the short wavelength observation mode is calculated by the following Equation M).

Brightness information for short wavelength observation mode=brightness adjustment coefficient $ktr \times R$ image signal+brightness adjustment coefficient $ktg \times G$ image signal+brightness adjustment coefficient $ktb \times B$ image signal+brightness adjustment coefficient $ktw \times W$ image signal      Equation M)

Since only the specific narrow-band light of the short wavelength is illuminated in the short wavelength observation mode, in the calculation of the brightness information for the short wavelength observation mode, only the B image signal and the W image signal having the pixel value corresponding to the specific narrow-band light of the short wavelength may be used. However, in the present embodiment, since the G pixel and the R pixel have the short-wavelength sensitivity, the G image signal and the R image signal are also used together in the calculation of the brightness information for the short wavelength observation mode.

In order to accurately calculate the brightness information for the short wavelength observation mode that corresponds to the illumination of only the specific narrow-band light of the short wavelength, it is preferable that the ratio between the brightness adjustment coefficient ktr (brightness adjustment coefficient for the fourth pixel), the brightness adjustment coefficient ktg (brightness adjustment coefficient for the second pixel), the brightness adjustment coefficient ktb (brightness adjustment coefficient for the first pixel), and the brightness adjustment coefficient ktw (brightness adjustment coefficient for the third pixel) is determined on the basis of the short-wavelength sensitivity of the R pixel, the G pixel, the B pixel, and the W pixel and the reflectance of the mucous membrane.

Here, in a case where Equation M) is used, when the spectral sensitivity of the W pixel is about 45% of the spectral sensitivity of the B pixel at 400 nm to 420 nm, and 15% to 20% of the spectral sensitivity of the G pixel and the R pixel at 400 nm to 420 nm, in consideration of the reflectance of the mucous membrane, it is preferable that the ratio between the brightness adjustment coefficient ktr, the brightness adjustment coefficient ktg, the brightness adjustment coefficient ktb, and the brightness adjustment coefficient ktw is set to "2:2:5:4".

The brightness information for the short wavelength observation mode is preferably calculated on the basis of at least two image signals of the B image signal and the G image signal. In a case where the brightness information for the short wavelength observation mode is calculated on the basis of the B image signal and the G image signal, the calculation is performed by Equation M1).

Brightness information for short wavelength observation mode=brightness adjustment coefficient $ktg \times G$ image signal+brightness adjustment coefficient $ktb \times B$ image signal      Equation M1)

Here, in a case where Equation M1) is used, when the spectral sensitivity of the G pixel at 400 nm to 420 nm is 15% to 20% of the spectral sensitivity of the B pixel at 400 nm to 420 nm, in consideration of the reflectance of the mucous membrane, it is preferable that the ratio between the brightness adjustment coefficient ktg and the brightness adjustment coefficient ktb is set to "2:5".

Further, in a case where the brightness information for the short wavelength observation mode is calculated on the basis of the B image signal, the G image signal, and the W image signal, the calculation is performed by Equation M2).

Brightness information for short wavelength observation mode=brightness adjustment coefficient $ktg \times G$ image signal+brightness adjustment coefficient $ktb \times B$ image signal+brightness adjustment coefficient $ktw \times W$ image signal      Equation M2)

Here, in a case where Equation M2) is used, when the spectral sensitivity of the W pixel is about 45% of the spectral sensitivity of the B pixel at 400 nm to 420 nm, in consideration of the reflectance of the mucous membrane, it is preferable that the ratio between the brightness adjustment coefficient ktg, the brightness adjustment coefficient ktb, and the brightness adjustment coefficient ktw is set to "2:5:4".

Further, in a case where the brightness information for the short wavelength observation mode is calculated on the basis of the B image signal, the G image signal, and the R image signal, the calculation is performed by Equation M3).

Brightness information for short wavelength observation mode=brightness adjustment coefficient $ktr \times R$ image signal+brightness adjustment coefficient $ktg \times G$ image signal+brightness adjustment coefficient $ktb \times B$ image signal      Equation M3)

Here, in a case where Equation M3) is used, when the spectral sensitivity of the G pixel and the R pixel at 400 nm to 420 nm is 15% to 20% of the spectral sensitivity of the B pixel at 400 nm to 420 nm, in consideration of the reflectance of the mucous membrane, it is preferable that the ratio between the brightness adjustment coefficient ktr, the brightness adjustment coefficient ktg, and the brightness adjustment coefficient ktb is set to "2:2:5".

The DSP 56 performs various kinds of signal processing, such as defect correction processing, offset processing, gain correction processing, linear matrix processing, or gamma conversion processing, on the received image signal. In the defect correction processing, a signal of a defective pixel of the image sensor 48 is corrected. In the offset processing, a dark current component is removed from the image signal subjected to the defect correction processing, and an accurate zero level is set. In the gain correction processing, a signal level is adjusted by multiplying the image signal after the offset processing by a specific gain. The linear matrix processing for improving the color reproducibility is performed on the image signal after the gain correction processing. After that, brightness and saturation are adjusted by the gamma conversion processing.

The demosaicing processing (also referred to as isotropic processing or synchronization processing) is performed on the image signal after the linear matrix processing in the demosaicing processing unit 56a. In the normal observation mode and the special observation mode, a signal of the color lacking in each pixel is generated by interpolation. By the demosaicing processing, all pixels have signals of RGB colors. For the demosaicing processing in a case where a color image sensor for obtaining an RGBW image signal is used, for example, the method disclosed in JP2011-055038A can be used.

Figure 18:
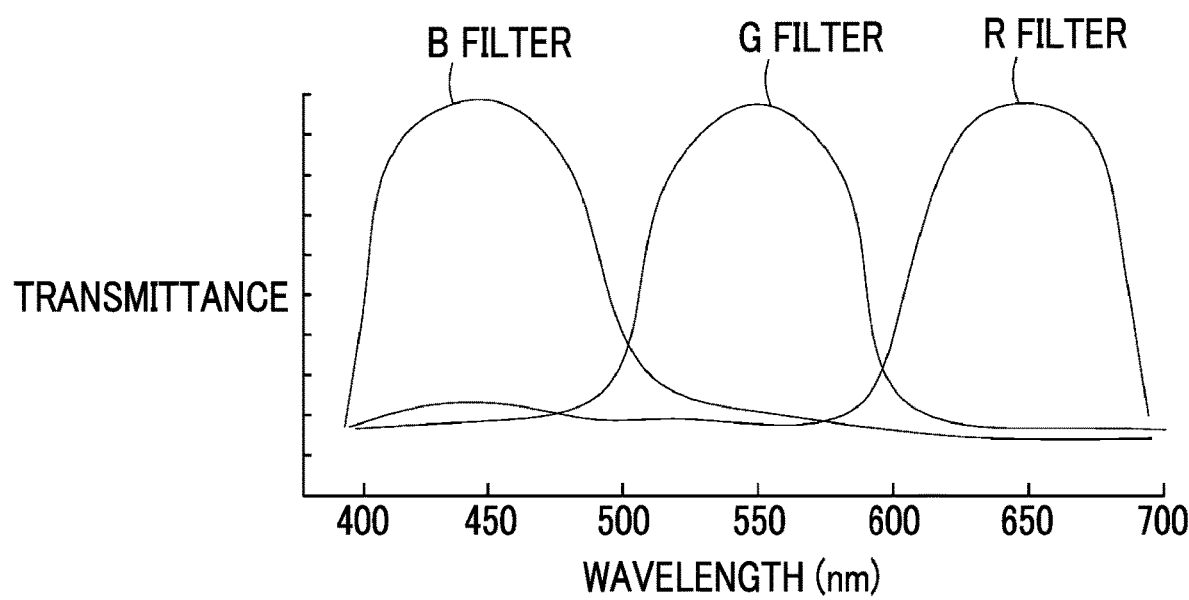
FIG. 18 is a graph showing spectral transmittances of a B filter, a G filter, and an R filter included in a normal image sensor.

In the short wavelength observation mode, the observation target is illuminated with only the specific narrow-band light of the short wavelength. However, in a normal RGB image sensor (an image sensor consisting of R pixels, G pixels, and B pixels), as shown in FIG. 18, the G filter and the R filter have almost no transmittance in the specific narrow-band, and the G pixel and the R pixel have almost no sensitivity to the specific narrow-band light. Therefore, in the short wavelength observation image obtained on the basis of the specific narrow-band light of the short wavelength, signals are obtained only from the B pixel and the W pixel having a sensitivity to specific narrow-band light, and almost no signals are obtained from the G pixel and the R pixel. For this reason, even if the demosaicing processing based on the correlation with the W pixel is performed, a short wavelength observation image with high resolution cannot be obtained. However, as shown in the present embodiment, by giving the G pixel and the R pixel the sensitivity to the specific narrow-band light, a constant signal corresponding to the specific narrow-band light can be obtained also from the G pixel and the R pixel, and therefore, a short wavelength observation image with high resolution can be obtained by the demosaicing processing based on the correlation with the W pixel. In the normal RGB image sensor, the G filter and the R filter have almost no transmittance in the blue band as shown in FIG. 18, so that the G pixel and the R pixel have almost no sensitivity in the blue band.

Hereinafter, in the short wavelength observation mode, by the signals obtained from the B pixel and the W pixel and the demosaicing processing based on the correlation with the W pixel, the signals obtained from the G pixel and the R pixel have a constant signal corresponding to the specific narrow-band light, and therefore, each signal is referred to as a short wavelength observation signal.

Figure 11:
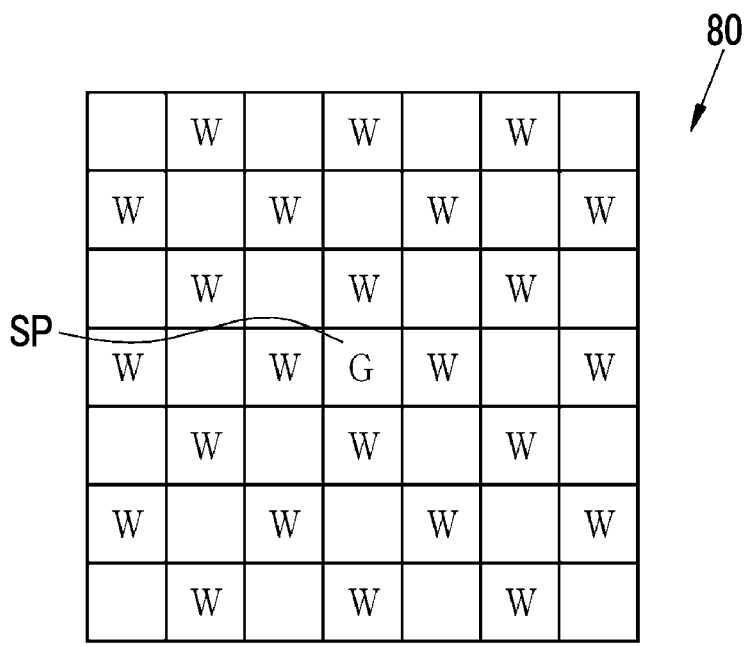
FIG. 11 is an explanatory diagram showing a G pixel located at a specific position SP in an image signal.
Figure 12:
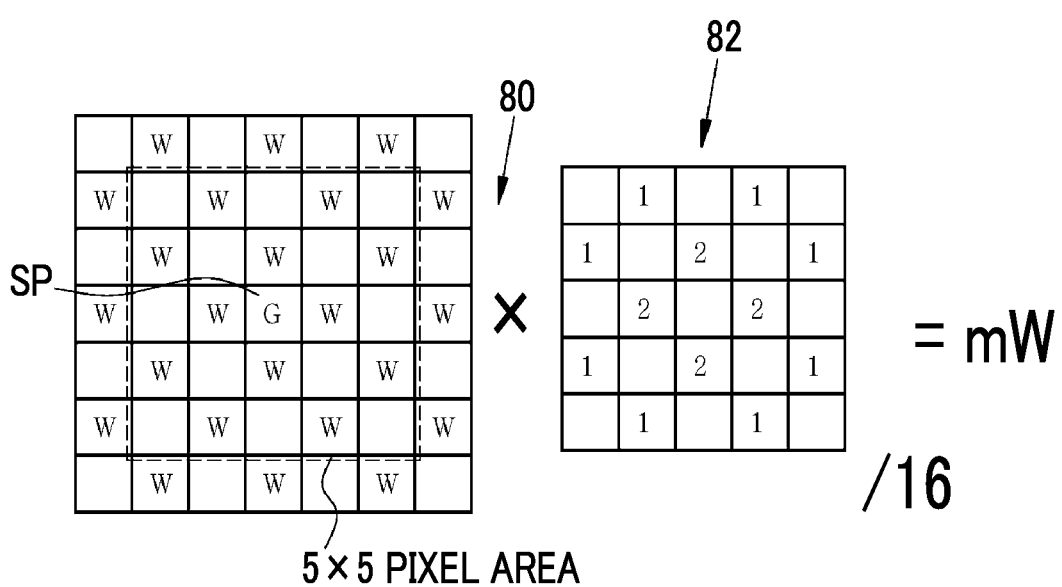
FIG. 12 is an explanatory diagram showing a method of calculating a low frequency component mW.

The method of calculating the pixel value of B pixel at the G pixel position as the short wavelength observation signal by the demosaicing processing based on the correlation with the pixel value of the W pixel is as follows. For example, as shown in FIG. 11, in an image signal 80 output from the image sensor 48, in a case of calculating a pixel value Bd of the B pixel at the G pixel position at a specific position SP, for discrete W pixel signals included in the image signal 80, W pixel values at all pixel positions are calculated by direction discrimination interpolation according to the neighboring W pixel values, image blur reduction processing for reducing image blur is performed on the calculated W pixel values by Wiener filter processing, and a W pixel signal (=Wd) after the image blur reduction processing (an image blur reduction processed signal) is calculated. Next, as shown in FIG. 12, by multiplying the pixel values of a 5×5 pixel area (a specific pixel area) by a first smoothing filter 82, a low frequency component mW (a first smooth-filtered component) is obtained. The first smoothing filter 82 is provided with a filter coefficient (such as "1" or "2") at the position where the W pixel is present in the image signal 80.

Figure 13:
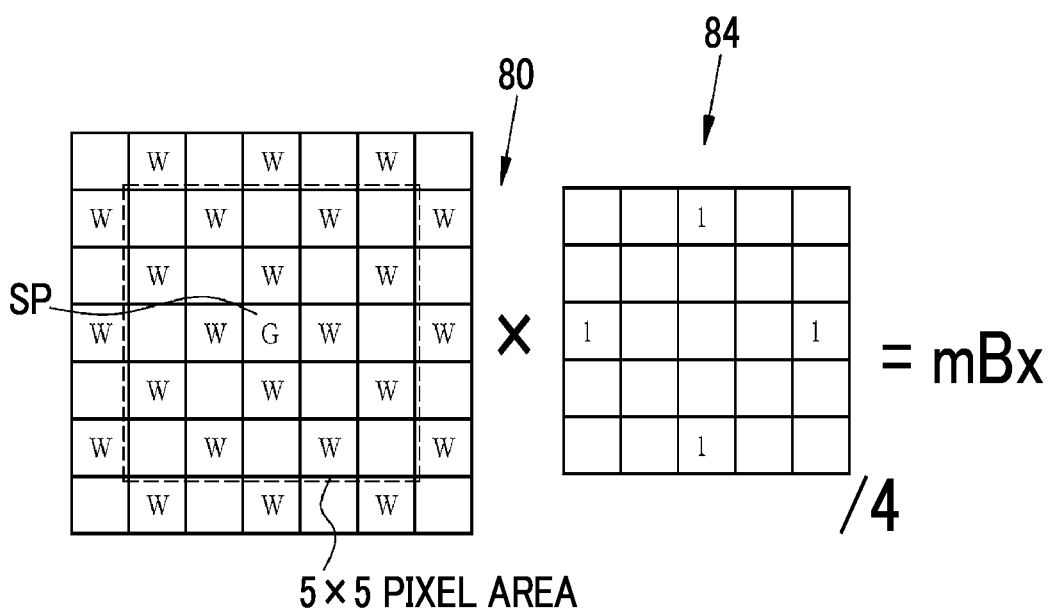
FIG. 13 is an explanatory diagram showing a method of calculating a low frequency component mBx.

Next, as shown in FIG. 13, by multiplying the pixel values of the 5×5 pixel area by a second smoothing filter 84, a low frequency component mBx (a second smooth-filtered component) is obtained. The second smoothing filter 84 is a filter that is applied to each 5×5 pixel area in which the G pixel is located at the specific position SP, and is provided with a filter coefficient (such as "1") at the position where the B pixel is present in the image signal 80. In the second smoothing filter 84, the filter coefficient setting is performed so that the pixel values of the B pixels at positions close to the specific position SP are evenly acquired. Then, the pixel value Bd of the B pixel at the G pixel position is calculated by the following Equation X).

$$Bd=(mBx/mW) \times Wd \qquad \text{Equation X)}$$

Figure 14:
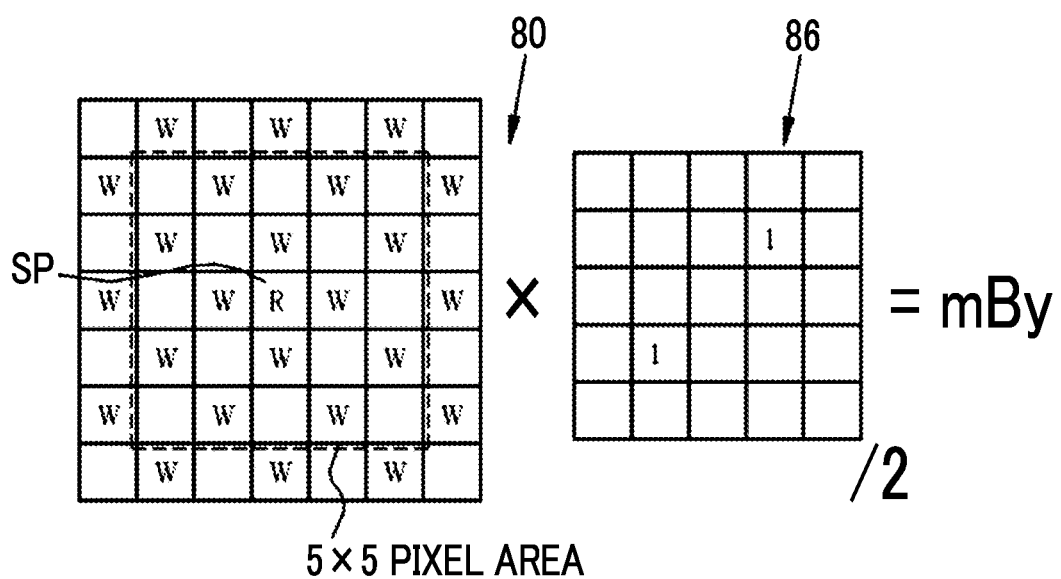
FIG. 14 is an explanatory diagram showing a method of calculating a low frequency component mBy.

The method of calculating the pixel value of B pixel at the R pixel position as the short wavelength observation signal by the demosaicing processing based on the correlation with the pixel value of the W pixel is as follows. Similar to the above case, a blur correction white (W) signal (=Wd) and the low frequency component mW are acquired. Then, as shown in FIG. 14, by multiplying the pixel values of the 5×5 pixel area by a third smoothing filter 86, a low frequency component mBy (a third smoothing filtered component) is acquired. The third smoothing filter 86 is a filter that is applied to each 5×5 pixel area in which the R pixel is located at the specific position SP, and is provided with a filter coefficient (such as "1") at the position where the B pixel is present in the image signal 80. Then, the pixel value Bd of the B pixel at the R pixel position is calculated by the following Equation Y).

$$Bd=(mBy/mW) \times Wd \qquad \text{Equation Y)}$$

The noise removal unit 58 removes noise from the RGB image signal by performing noise removal processing (for example, a moving average method or a median filter method) on the image signal that has been subjected to gamma correction or the like by the DSP 56. The image signal from which the noise has been removed is transmitted to the image processing unit 60.

The image processing unit 60 performs image processing corresponding to each observation mode. As an image processing method, for example, there is a method in which image processing parameters such as gradation processing and saturation enhancement corresponding to each observation mode are prepared, and the image signal is multiplied by the image processing parameters according to each observation mode. In the case of the normal observation mode, the RGB image signal is multiplied by a parameter for the normal observation mode, and in the case of the special observation mode, the RGB image signal is multiplied by a parameter for the special observation mode. In the case of the short wavelength observation mode, the B image signal is multiplied by a parameter for the short wavelength observation mode. The parameter for the normal observation mode, the parameter for the special observation mode, and the parameter for the short wavelength observation mode described above are switched by the parameter switching unit 62 in accordance with the mode switching of the mode switching SW 13a.

The display control unit 64 performs control for displaying an image signal input from the image processing unit 60 as an image that can be displayed on the monitor 18. In the case of the normal observation mode, a normal image is displayed on the monitor 18 by assigning the R image signal to the R channel of the monitor 18, the G image signal to the G channel of the monitor 18, and the B image signal to the B channel of the monitor 18. In the case of the special observation mode, a special observation image is displayed on the monitor 18 by assigning the G image signal to the R channel of the monitor 18, and the B image signal to the G channel and the B channel of the monitor 18 (in assigning, it is preferable to perform gradation processing and saturation enhancement). On the other hand, in the case of the short wavelength observation mode, a short wavelength observation image is displayed on the monitor 18 by assigning the short wavelength observation signal to each of the R, G, and B channels of the monitor 18. In assigning the short wavelength observation signal, the short wavelength observation image is multiplied by a gain for each of the R, G, and B channels, and the like, and then assigned to each channel. In this manner, the short wavelength observation image showing a structure that can be observed with specific narrow-band light of a short wavelength can be displayed on the monitor 18 as an image having a specific background color in which the structure of blood vessels and the like has better visibility than a gray image.

Second Embodiment

In the first embodiment, the RGBW image sensor is used as the image sensor 48, but as shown in FIG. 15, an image sensor having a Bayer array in which the ratio between the number of pixels of G pixels, B pixels, and R pixels is 2:1:1 may be used. In a case where the image sensor having a Bayer array is used, as demosaicing processing in the short wavelength observation mode for obtaining monochrome B image signals at all pixel positions, it is preferable to calculate a pixel value Bg of the B pixel at the G pixel position and a pixel value Br of the B pixel at the R pixel position as follows.

For example, as shown in FIG. 16, in a case of calculating a pixel value Bg(22) of the B pixel at the pixel position of the G pixel (G22) at the specific position SP, the calculation is performed by Equation Z1).

$$Bg(22)=G22\times 2(B21+B23)/(G11+G13+G31+G33) \quad \text{Equation Z1)}$$

According to Equation Z1), not only the pixel value of the B pixel around the specific position SP but also the pixel value of the G pixel is used, so that a more realistic pixel value of Bg(22) can be obtained.

Figure 17:
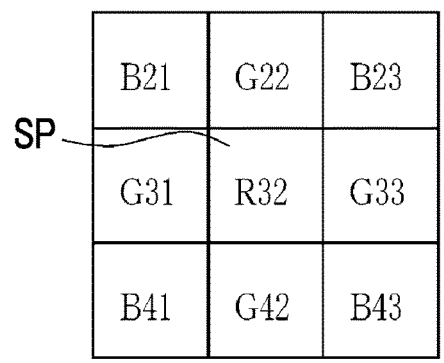
FIG. 17 is an explanatory diagram used for describing a method of calculating a pixel value of a B pixel at an R pixel position in the image sensor having a Bayer array.

Note that, as shown in FIG. 17, in a case of calculating a pixel value Br(32) of the B pixel at the pixel position of the R pixel (R32) at the specific position SP, the calculation is performed by Equation Z2).

$$Br(32)=(B21+B23+B41+B43)/4 \quad \text{Equation Z2)}$$

In the first and second embodiments, in the demosaicing processing in the short wavelength observation mode, the pixel value (B image signal) of the B pixel at the G pixel position and the R pixel position is calculated; however, similarly to the normal observation mode or the special observation mode, the pixel value of each of the R pixel, G pixel, and B pixel at each pixel position may be calculated.

In the embodiment, the hardware structure of the processing units included in the processor device 16, such as the image acquisition unit 53, the brightness information calculation unit 54, the DSP 56, the noise removal unit 58, the image processing unit 60, the parameter switching unit 62, and the display control unit 64 is various processors as follows. The various processors include a central processing unit (CPU) that is a general-purpose processor that functions as various processing units by executing software (program), a programmable logic device (PLD) that is a processor whose circuit configuration can be changed after manufacture, such as field programmable gate array (FPGA), a dedicated electrical circuit that is a processor having a circuit configuration designed exclusively for executing various types of processing, and the like.

One processing unit may be configured by one of various processors, or may be configured by a combination of two or more processors of the same type or different types (for example, a combination of a plurality of FPGAs or a combination of a CPU and an FPGA). In addition, a plurality of processing units may be configured by one processor. As an example of configuring a plurality of processing units by one processor, first, as represented by a computer, such as a client or a server, there is a form in which one processor is configured by a combination of one or more CPUs and software and this processor functions as a plurality of processing units. Second, as represented by a system on chip (SoC) or the like, there is a form of using a processor for realizing the function of the entire system including a plurality of processing units with one integrated circuit (IC) chip. Thus, various processing units are configured by using one or more of the above-described various processors as hardware structures.

More specifically, the hardware structure of these various processors is an electrical circuit (circuitry) in the form of a combination of circuit elements, such as semiconductor elements.

In the embodiment, the invention is applied to the endoscope system that performs processing on the endoscopic image as one of the medical images. However, the invention can also be applied to a medical image processing system that processes medical images other than the endoscopic image.

EXPLANATION OF REFERENCES

10: endoscope system
12: endoscope
12a: insertion part
12b: operation part
12c: bendable portion
12d: distal end portion
12e: angle knob
13a: mode switching SW
13b: still image acquisition instruction part
14: light source device
16: processor device
18: monitor
19: user interface
20: light source unit
20a: violet light emitting diode (V-LED)
20b: blue light emitting diode (B-LED)
20c: green light emitting diode (G-LED)
20d: red light emitting diode (R-LED)
21: light source control unit
23: optical path coupling unit
30a: illumination optical system
30b: imaging optical system
41: light guide
45: illumination lens
46: objective lens
48: image sensor
50: CDS/AGC circuit
52: A/D converter
53: image acquisition unit
54: brightness information calculation unit
56: digital signal processor (DSP)
56a: demosaicing processing unit
58: noise removal unit
60: image processing unit
62: parameter switching unit
64: display control unit
80: image signal
82: first smoothing filter
84: second smoothing filter
86: third smoothing filter

What is claimed is:

1. A medical image processing system comprising:
   a light source unit that emits specific narrow-band light of a short wavelength;
   an image sensor that images an observation target illuminated with the specific narrow-band light, the image sensor including a first pixel group including a first pixel and a second pixel group including at least a second pixel; and
   a light source control circuit that controls a light emission amount of the specific narrow-band light,
   wherein the first pixel has a higher sensitivity to the specific narrow-band light than the second pixel,
   the second pixel has a sensitivity to first long-wavelength light of a longer wavelength than the specific narrow-band light and the specific narrow-band light, and
   the light source control circuit controls the light emission amount of the specific narrow-band light on the basis of a pixel value of the first pixel obtained in the first pixel and a pixel value of the second pixel obtained in the second pixel.

2. The medical image processing system according to claim 1,
wherein the second pixel group includes a third pixel having a sensitivity to broadband illumination light including the specific narrow-band light and the first long-wavelength light, and
the light source control circuit controls the light emission amount of the specific narrow-band light on the basis of a pixel value of the third pixel in addition to the pixel value of the first pixel and the pixel value of the second pixel.

3. The medical image processing system according to claim 1,
wherein the second pixel group includes a fourth pixel having a sensitivity to second long-wavelength light of a longer wavelength than the first long-wavelength light and the specific narrow-band light, and
the light source control circuit controls the light emission amount of the specific narrow-band light on the basis of a pixel value of the fourth pixel in addition to the pixel value of the first pixel and the pixel value of the second pixel.

4. The medical image processing system according to claim 1, further comprising:
a processor configured to calculate brightness information indicating brightness of the observation target on the basis of the pixel value of the first pixel multiplied by a brightness adjustment coefficient for the first pixel and the pixel value of the second pixel multiplied by a brightness adjustment coefficient for the second pixel,
wherein the light source control circuit controls the light emission amount of the specific narrow-band light on the basis of the brightness information, and
a ratio between the brightness adjustment coefficient for the first pixel and the brightness adjustment coefficient for the second pixel is determined on the basis of a short-wavelength sensitivity to short-wavelength light including the specific narrow-band light in the sensitivity of the first pixel and the short-wavelength sensitivity of the second pixel.

5. The medical image processing system according to claim 4,
wherein the short-wavelength sensitivity of the second pixel is 10% or more of a maximum sensitivity of the second pixel, or 10% or more of the short-wavelength sensitivity of the first pixel.

6. The medical image processing system according to claim 4,
wherein the short-wavelength sensitivity of the second pixel is 35% or less of a maximum sensitivity of the second pixel, or 35% or less of the short-wavelength sensitivity of the first pixel.

7. The medical image processing system according to claim 2, further comprising:
a processor configured to calculate brightness information indicating brightness of the observation target on the basis of the pixel value of the first pixel multiplied by a brightness adjustment coefficient for the first pixel, the pixel value of the second pixel multiplied by a brightness adjustment coefficient for the second pixel, and the pixel value of the third pixel multiplied by a brightness adjustment coefficient for the third pixel,
wherein the light source control circuit controls the light emission amount of the specific narrow-band light on the basis of the brightness information, and
a ratio between the brightness adjustment coefficient for the first pixel, the brightness adjustment coefficient for the second pixel, and the brightness adjustment coefficient for the third pixel is determined on the basis of a short-wavelength sensitivity to short-wavelength light including the specific narrow-band light in the sensitivity of the first pixel, the short-wavelength sensitivity of the second pixel, and the short-wavelength sensitivity of the third pixel.

8. The medical image processing system according to claim 3, further comprising:
a processor configured to calculates brightness information indicating brightness of the observation target on the basis of the pixel value of the first pixel multiplied by a brightness adjustment coefficient for the first pixel, the pixel value of the second pixel multiplied by a brightness adjustment coefficient for the second pixel, and the pixel value of the fourth pixel multiplied by a brightness adjustment coefficient for the fourth pixel,
wherein the light source control circuit controls the light emission amount of the specific narrow-band light on the basis of the brightness information, and
a ratio between the brightness adjustment coefficient for the first pixel, the brightness adjustment coefficient for the second pixel, and the brightness adjustment coefficient for the fourth pixel is determined on the basis of a short-wavelength sensitivity to short-wavelength light including the specific narrow-band light in the sensitivity of the first pixel, the short-wavelength sensitivity of the second pixel, and the short-wavelength sensitivity of the fourth pixel.

9. The medical image processing system according to claim 1,
wherein the number of pixels of the second pixel group is greater than the number of pixels of the first pixel group.

10. The medical image processing system according to claim 2,
wherein the number of pixels of the second pixel group is greater than the number of pixels of the first pixel group.

11. The medical image processing system according to claim 3,
wherein the number of pixels of the second pixel group is greater than the number of pixels of the first pixel group.

12. The medical image processing system according to claim 4,
wherein the number of pixels of the second pixel group is greater than the number of pixels of the first pixel group.

13. The medical image processing system according to claim 5,
wherein the number of pixels of the second pixel group is greater than the number of pixels of the first pixel group.

14. The medical image processing system according to claim 6,
wherein the number of pixels of the second pixel group is greater than the number of pixels of the first pixel group.

15. The medical image processing system according to claim 1, wherein a center wavelength of the specific narrow-band light is included in a range of 400 nm to 450 nm, and a half-width of the specific narrow-band light is 40 nm or less.

16. The medical image processing system according to claim 2,
wherein a center wavelength of the specific narrow-band light is included in a range of 400 nm to 450 nm, and a half-width of the specific narrow-band light is 40 nm or less.

17. The medical image processing system according to claim 3,
wherein a center wavelength of the specific narrow-band light is included in a range of 400 nm to 450 nm, and a half-width of the specific narrow-band light is 40 nm or less.

18. The medical image processing system according to claim 4,
wherein a center wavelength of the specific narrow-band light is included in a range of 400 nm to 450 nm, and a half-width of the specific narrow-band light is 40 nm or less.

19. The medical image processing system according to claim 5,
wherein a center wavelength of the specific narrow-band light is included in a range of 400 nm to 450 nm, and a half-width of the specific narrow-band light is 40 nm or less.

20. The medical image processing system according to claim 6,
wherein a center wavelength of the specific narrow-band light is included in a range of 400 nm to 450 nm, and a half-width of the specific narrow-band light is 40 nm or less.

* * * * *